US009248273B2

(12) United States Patent
Guvanasen et al.

(10) Patent No.: US 9,248,273 B2
(45) Date of Patent: Feb. 2, 2016

(54) 3D MICROELECTRODE DEVICE FOR LIVE TISSUE APPLICATIONS

(71) Applicants: Axion Biosystems, Inc., Atlanta, GA (US); Georgia Institute of Technology, Atlanta, GA (US)

(72) Inventors: Gareth S. Guvanasen, Herndon, VA (US); Swaminathan Rajaraman, Atlanta, GA (US); Ricardo Aguilar, Jr., Lillburn, GA (US); Liang Guo, Cambridge, MA (US); T. Richard Nichols, Atlanta, GA (US); Stephen P. DeWeerth, Mendota, IL (US)

(73) Assignees: Axion Biosystems, Inc., Atlanta, GA (US); Georgia Tech Research Corporation, Atlanta, GA (US)

( * ) Notice: Subject to any disclaimer, the term of this patent is extended or adjusted under 35 U.S.C. 154(b) by 56 days.

(21) Appl. No.: 13/919,013

(22) Filed: Jun. 17, 2013

(65) Prior Publication Data
US 2013/0338746 A1   Dec. 19, 2013

Related U.S. Application Data

(60) Provisional application No. 61/660,876, filed on Jun. 18, 2012.

(51) Int. Cl.
*A61N 1/05* (2006.01)
*A61B 5/04* (2006.01)
(Continued)

(52) U.S. Cl.
CPC .......... *A61N 1/0502* (2013.01); *A61B 5/04001* (2013.01); *A61B 5/0492* (2013.01);
(Continued)

(58) Field of Classification Search
CPC . A61N 1/502; A61N 1/0551; A61B 5/04001; A61B 5/0492; A61B 2562/164; A61B 2562/0209; A61B 2562/125; H05K 1/095; H05K 1/0283; H05K 2201/10318; H05K 2201/0245
USPC .................... 607/116; 264/272.11; 156/272.6
See application file for complete search history.

(56) References Cited

U.S. PATENT DOCUMENTS

2006/0074460 A1   4/2006   Maghribi et al.
2007/0231850 A1*  10/2007  Geoffrey et al. ................ 435/29
2011/0254171 A1   10/2011  Guo et al.

FOREIGN PATENT DOCUMENTS

KR   101054864 B1   8/2011
WO   2011/157714 A1   12/2011

OTHER PUBLICATIONS

Wang, R. et al., "A Flexible Microneedle Electrode Array With Solid Silicon Needles," Journal of Microelectromechanical Systems, vol. 21, No. 5, pp. 1084-1089, Oct. 2012.

(Continued)

*Primary Examiner* — Alyssa M Alter
(74) *Attorney, Agent, or Firm* — Meunier Carlin & Curfman LLC

(57) ABSTRACT

A 3D microelectrode device includes a flexible substrate containing poly-dimethyl siloxane (PDMS). The device may be fabricated in a miniature form factor suitable for attachment to a small organ such as a lateral gastrocnemius muscle of a live rat. In addition to providing a miniaturized, conformable attachment, the device provides an anchoring action via one or more microelectrodes, each having an insertable tip particularly shaped to provide the anchoring action. Furthermore, a base portion of each of the microelectrodes is embedded inside conductive poly-dimethyl siloxane (cPDMS). The cPDMS is contained in a pad that is coupled to a conductive track embedded in the flexible substrate. Embedding of the base portion inside the cPDMS material not only allows the microelectrode to bend in various directions, but also provides good electrical conductivity while eliminating the need for attachment processes using solder or epoxy adhesives.

18 Claims, 10 Drawing Sheets

(51) Int. Cl.
*A61B 5/0492* (2006.01)
*H05K 1/09* (2006.01)
*H05K 1/02* (2006.01)

(52) U.S. Cl.
CPC .............. *A61N1/0551* (2013.01); *H05K 1/095* (2013.01); *A61B 2562/0209* (2013.01); *A61B 2562/125* (2013.01); *A61B 2562/164* (2013.01); *H05K 1/0283* (2013.01); *H05K 2201/0245* (2013.01); *H05K 2201/10318* (2013.01)

(56) References Cited

OTHER PUBLICATIONS

Guo, L. et al., "A PDMS-Based Integrated Stretchable Microelectrode Array (isMEA) for Neural and Muscular Surface Interfacing," IEEE Trans. on Biomed. Circuits and Syst., vol. 7, No. 1, pp. 1-10, Feb. 2013.
Lapatki, B.G. et al., "A thin, flexible multielectrode grid for high-density surface EMG," J. Appl. Physiol., vol. 96, pp. 327-336, 2004.
Palchesko, R.N. et al., "Development of Polydimethylsiloxane Substrates with Tunable Elastic Modulus to Study Cell Mechanobiology in Muscle and Nerve," PLoS One, vol. 7, No. 12, pp. 1-13, Dec. 2012.
Agar, J.C. et al., "Novel PDMS(silicone)-in-PDMS(silicone): Low Cost Flexible Electronics without Metallization," 2010 Electronic Components and Technology Conference, pp. 1226-1230, 2010.
Zhang, R. et al., "A simple, low-cost approach to prepare flexible highly conductive polymer composites by in situ reduction of silver carboxylate for flexible electronic applications," Compos. Sci. and Technol., vol. 71, pp. 528-534, 2011.
"Silver Flake #15ED," Ferro Corporation, Plainfield, NJ, pp. 1-2, 1999.
"Enliten® ATP Assay System Bioluminescence Detection Kit for ATP Measurement," Promega Corporation, Madison, WI, pp. 1-7, 2009.
Viventi, J. et al., "Flexible, foldable, actively multiplexed, high-density electrode array for mapping brain activity in vivo," Nature Neuroscience, vol. 14, No. 12, 2011.
Bosetti, M. et al., "Silver coated materials for external fixation devices: in vitro biocompatibility and genotoxicity," Biomaterials, vol. 23, pp. 887-892, 2002.
Niu, X. et al., "Characterizing and Patterning of PDMS-Based Conducting Composites," Advanced Materials, vol. 19, pp. 2682-2686, 2007.
International Search Report in PCT/US2013/046104, mailed Jan. 31, 2014.
Written Opinion of the International Searching Authority in PCT/US2013/046104, mailed Jan. 31, 2014.
Wei, P. et al., "Stretchable microelectrode array using room-temperature liquid alloy interconnects," J. of Micromechanics and Microengineering, vol. 21, No. 5, 2011.
Lacour, S.P. et al., "Flexible and stretchable micro-electrodes for in vitro and in vivo neural interfaces," Medical & Biological Engineering & Computing, vol. 48, No. 10, pp. 945-954, 2010.

\* cited by examiner

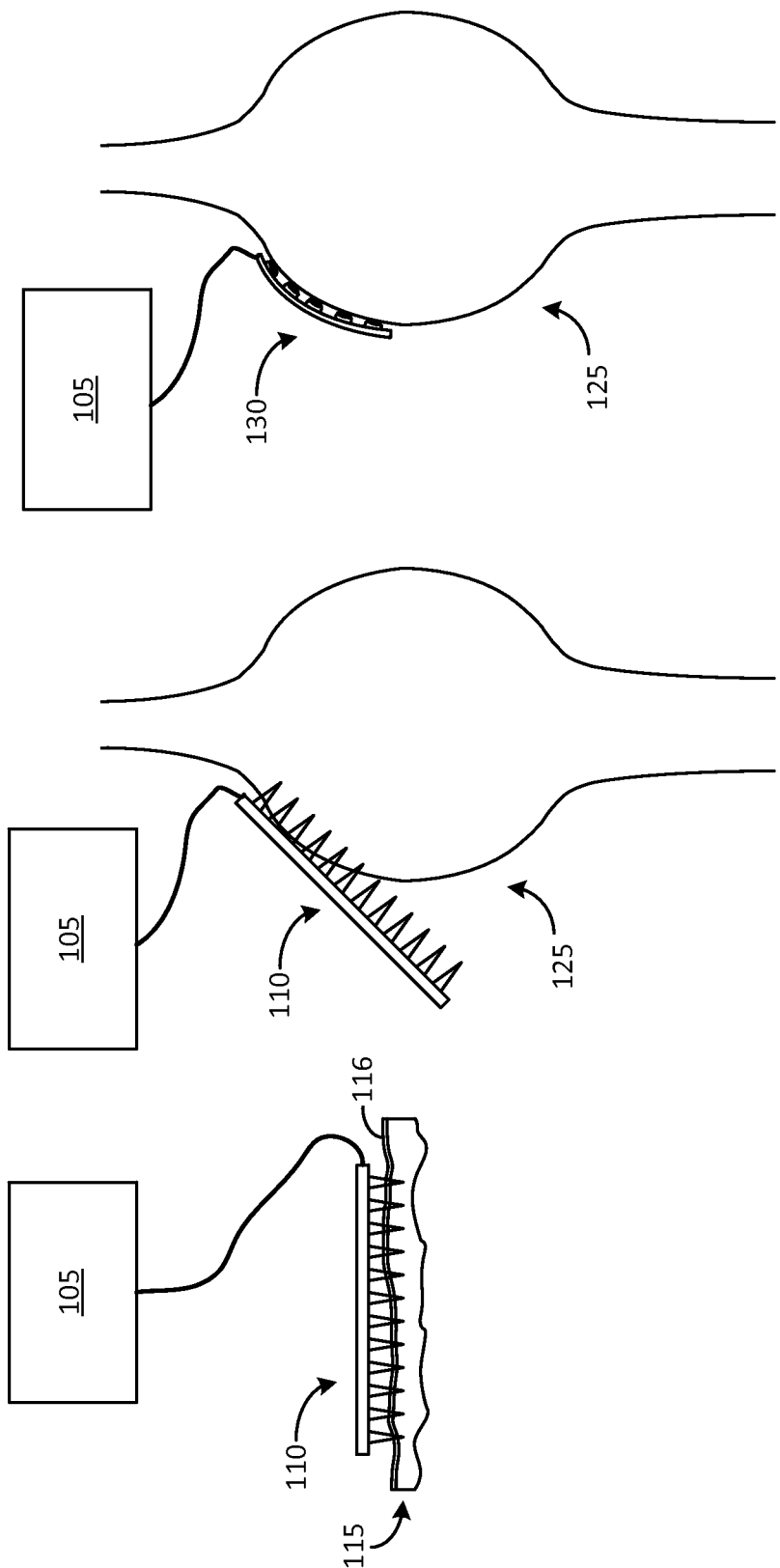

3D MICROELECTRODE DEVICE FOR LIVE TISSUE APPLICATIONS

CROSS-REFERENCE

This application claims the benefit of priority to U.S. Provisional Application Ser. No. 61/660,876, filed Jun. 18, 2012, which is incorporated herein by reference in its entirety and for all purposes

STATEMENT REGARDING FEDERALLY SPONSORED RESEARCH OR DEVELOPMENT

This invention was made with government support under grant NS071894-01 awarded by the National Institute of Health. The government has certain rights in the invention.

BACKGROUND

Approximately 62 million people in this world are estimated to have some form of paralysis, and approximately 10 million people are estimated to have received an amputation. One of the techniques utilized to afford greater mobility to amputees is myoelectric prosthesis. Myoelectric prosthesis typically involves the measurement of electrical activity in a contracting muscle located close to the site of the paralysis/amputation and using the measurement to provide suitable electrical stimuli to the paralyzed muscle or to residual functioning muscle. In essence, myoelectric prosthesis enables individuals to control a paralyzed muscle (or robotic prosthetics) through a residual functioning muscle. Unfortunately, the degree of motor function returned via myoelectric prosthesis is limited, largely due to the prosthetic's inability to extract sufficient information from a working muscle or to adequately control paralyzed muscle via electrical stimulation. Furthermore, existing devices and techniques used for performing myoelectric prosthesis suffer from various limitations.

To elaborate upon a first limitation, attention is drawn to a first prior art reference document titled "*Microelectrodes with Three-dimensional Structures for Improved Neural Interfacing*," by S. Metz et al, and further to a second prior art reference document titled "*A Three-Dimensional Multi-electrode Array for Multi-site Stimulation and Recording in Acute Brain Slices*," by Marc Olive Heuschkel et. al.

The teachings in these two prior art reference documents may be summarized using FIG. 1 that is shown herein in this disclosure.

Prior art microelectrode device 110, which is coupled to an electrical stimulus transmitter/response signal receiver 105, contains a number of microelectrodes that are mounted on a rigid glass substrate and are shaped for penetrating a tissue slice 115. More particularly, the microelectrodes are pyramid-shaped microelectrodes that are allegedly advantageous for penetrating dead cell layer 116 and getting closer to active cells located below dead cell layer 116.

While microelectrode device 110 does provide certain advantages for in-vitro applications, the rigid nature of the glass substrate and the size of the device (for example, a 60 microelectrode device is shown to have a size of 5×5 cm$^2$) make this prior art device unsuitable for many in-vivo applications, especially when it is desired to implant such a device upon a small-sized live organ, live muscle or live tissue.

This aspect is illustrated in FIG. 2. When microelectrode device 110 is implanted upon organ 125, which may be an internal organ of a rat for example, the rigid nature of the substrate and the size of the device 110 permit only a few of the microelectrodes from penetrating the outer layer of organ 125. Furthermore, it can be understood that the projecting portion of device 110 may make undesirable contact with adjacent organs (not shown) and may potentially cause damage to these adjacent organs.

The disadvantages described above with reference to prior art microelectrode device 110 are alleviated to some extent by a different prior art microelectrode device 130 that is disclosed in a third prior art reference document titled "*PDMS-Based Stretchable Multi-Electrode and Chemotrode Array for Epidural and Subdural Neuronal Recording, Electrical Stimulation and Drug Delivery*" (International Publication Number WO 2011/157714 A1).

As shown in FIG. 3, device 130 not only incorporates a flexible substrate that conforms to a surface layer of organ 125, but also includes certain features that are allegedly advantageous for in-vivo applications wherein placement of the microelectrodes to the proximity of an organ, such as the spinal cord of a rat, is desirable. As described in the third prior art reference document, the non-penetrating nature of the microelectrodes makes the implantation less invasive and less traumatic—thereby teaching away from the use of penetrating microelectrodes such as those disclosed in the first and second prior art reference documents.

More particularly, device 130 is placed such that surrounding tissue material (dura matter for example) located above and below device 130, provides an anchoring action to keep device 130 in place without damaging the spinal cord. The lack of an intrinsic anchoring element in device 130 makes it difficult or impossible to use device 130 upon certain tissue surfaces where surrounding tissue or other structures are unavailable to hold device 130 in place.

Furthermore, the size and shape of the spinal cord necessitates that device 130 have a relatively large and elongated shape (together with relatively large dimensions for pads, tracks, holes etc.). In this context, it may be pertinent to draw attention to FIGS. 11 and 12 of the third prior art reference document and the associated description, which discloses a conductive track width of 150 μm, minimum distance between adjacent tracks if 150 μm, diameter of each microelectrode is 350 μm, and holes of 350 μm diameter. While such dimensions may be acceptable for mounting on to relatively large organs, these dimensions are not suitable for use when the organ is very small in size.

In view of the above-mentioned remarks, it would be desirable to make certain improvements to existing microelectrode devices.

SUMMARY

According to a first aspect of the disclosure, a device that includes a flexible substrate, a track and a microelectrode is provided. The flexible substrate is configured to provide three-dimensional conformance with a live tissue surface susceptible to movement. The track, which contains conductive poly-dimethyl siloxane (cPDMS) material, is embedded in the flexible substrate for conducting an electrical signal. The microelectrode has a base portion, a longitudinal portion, and an insertable tip. The base portion has a shape configured for anchoring the base portion in the cPDMS material and the insertable tip has a leading portion configured for penetrating the tissue surface and making contact with a muscle located below the tissue surface.

According to a second aspect of the disclosure, an implantable device that includes a flexible substrate, a plurality of signal-conducting tracks, and a plurality of microelectrodes is provided. The flexible substrate is configured to provide three-dimensional conformance with an in-vivo surface that is susceptible to flexing. The plurality of signal-conducting tracks is embedded in the flexible substrate, each of the plurality of tracks comprising conductive poly-dimethyl siloxane (cPDMS) material. The plurality of microelectrodes is arranged in an array configuration, each of the plurality of microelectrodes comprising a base portion and a protruding portion. The base portion has a shape configured for anchoring the microelectrode in the cPDMS material, and the protruding portion has a shape configured for penetrating the in-vivo surface and for anchoring the implantable device upon the in-vivo surface According to a third aspect of the disclosure, a method of manufacturing a 3D microelectrode device includes the following: applying a layer of SU-8 upon a silicon substrate; using lithography to define a layout pattern in the SU-8 layer; developing the SU-8 layer, the developing directed at creating at least 1) a first indentation corresponding to a track in the layout pattern and 2) a second indentation corresponding to a pad in the layout pattern; applying a layer of metal upon the developed SU-8 layer; applying a layer of conductive poly-dimethyl siloxane (cPDMS) material on top of the layer of metal such that the cPDMS material fills the first and second indentations; placing a 3D microelectrode in an upright position in the second indentation, a base portion of the 3D microelectrode operative to anchoring the microelectrode in the cPDMS material; curing the assembly for encapsulating at least the base portion of the 3D microelectrode in the cPDMS material; applying a layer of poly-dimethyl siloxane (PDMS) material on top of the cured cPDMS material; and removing the silicon substrate by demolding, whereby the remaining portion that includes the cPDMS material, the 3D microelectrode, and the PDMS material constitutes at least a part of the 3D microelectrode device.

According to a fourth aspect of the disclosure, a method of manufacturing a microelectrode apparatus, includes the following: applying a layer of photoresist upon a silicon substrate; using photolithography to define a layout pattern in the photoresist layer; developing the photoresist layer; etching the silicon substrate for creating at least 1) a first indentation corresponding to a track and 2) a second indentation corresponding to a pad in the layout pattern; applying a layer of metal upon the developed photo-resist layer; applying a layer of conductive poly-dimethyl siloxane (cPDMS) material on top of the layer of metal such that the cPDMS material fills the first and second indentations; placing a microelectrode in an upright position in the second indentation, a base portion of the microelectrode operative to anchoring the microelectrode in the cPDMS material; curing the assembly for encapsulating the microelectrode in the cPDMS material; applying a layer of poly-dimethyl siloxane (PDMS) material on top of the cured cPDMS material; and removing the silicon substrate by demolding, the remaining portion that includes the cPDMS material, the microelectrode, and the PDMS material constituting at least a part of the microelectrode apparatus.

Further aspects of the disclosure are shown in the specification, drawings and claims below.

BRIEF DESCRIPTION OF THE DRAWINGS

Many aspects of the invention can be better understood with reference to the following drawings. The components in the drawings are not necessarily to scale. Instead, emphasis is placed upon clearly illustrating the principles of the invention. Moreover, in the drawings, like reference numerals designate corresponding parts, or descriptively similar parts, throughout the several views and embodiments.

FIG. 1 shows a first prior art microelectrode device used in an in-vitro application.

FIG. 2 shows the first prior art microelectrode device used in an in-vivo application.

FIG. 3 shows a second prior art microelectrode device used in an in-vivo application.

DETAILED DESCRIPTION

Throughout this description, embodiments and variations are described for the purpose of illustrating uses and implementations of the inventive concept. The illustrative description should be understood as presenting examples of the inventive concept, rather than as limiting the scope of the concept as disclosed herein. For example, it will be understood that terminology such as upper, lower, top, bottom, pins, pads, and tracks are used herein as a matter of convenience for description purposes and should not be interpreted in a limiting manner. As one can appreciate, the word "upper" used in a first context may be referred to as "lower" in a different context, and consequently, such terms should be interpreted solely to understand the invention rather than to circumvent it, for example, by flipping an object upside down, or mirroring the object.

It must also be understood that the word "example" as used herein (in whatever context) is intended to be non-exclusionary and non-limiting in nature. Specifically, the word "exemplary" when used indicates one among several examples, and it must be understood that no special emphasis is intended or suggested for that particular example. A person of ordinary skill in the art will understand the principles described herein and recognize that these principles can be applied to a wide variety of devices and applications.

The various embodiments disclosed here in accordance with the invention generally describe a 3D microelectrode device that may be used for live tissue applications. While live tissue is typically associated with in-vivo applications, it must be understood that the various embodiments are not limited to in-vivo applications and may be used for in-vitro applications as well.

Furthermore, while reference is made herein to materials generically known in the art as poly-dimethyl siloxane (PDMS) and conductive poly-dimethyl siloxane (cPDMS), it must be understood that the various embodiments disclosed herein may incorporate a specific formulation, composition, manufacture, and application of PDMS and cPDMS. These aspects will be described below in further detail.

PDMS has many desirable characteristics such as being bio-compatible, being compatible for large area microfabrication, and possessing a Young's modulus at least three orders of magnitude lower than materials such as silicon and polyimide that are used in various prior art intramuscular microelectrode arrays. Due to the Young's modulus property alone, PDMS has the potential to cause less scar-tissue encapsulation and may be applied across a large interfacial area.

Associated with PDMS is a compound referred to as cPDMS, which is manufactured by dispersing conductive metal flakes in a PDMS polymer. When cPDMS is used in the form of electrically conductive tracks or pads, the cPDMS conductive tracks and pads maintain a high conductivity/low resistance characteristic even under a relatively high degree of tensile strain.

Figure 4:
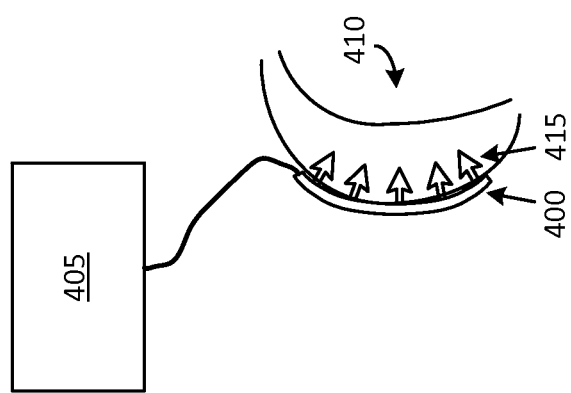
FIG. 4 shows an exemplary in-vivo application of a 3D microelectrode device in accordance with an embodiment of the present invention.

Attention is now drawn to FIG. 4, which shows an example embodiment of a 3D microelectrode device 400 in accordance with an embodiment of the present invention. 3D microelectrode device 400, which may be coupled to an electrical stimulus transmitter and/or response signal receiver 405, is shown conformably attached to a small internal organ 410, such as a lateral gastrocnemius muscle of a rat (thereby illustrating the miniature size of an embodiment of the present invention).

In addition to providing a miniaturized, conformable attachment, 3D microelectrode device 400 also provides an anchoring action via a microelectrode array 415 containing a number of microelectrodes each having a shape that is specifically selected to provide the anchoring action. This aspect will be described below in further detail.

A base portion of each of the microelectrodes in microelectrode array 415 is embedded inside conductive poly-dimethyl siloxane (cPDMS) thereby providing good electrical conductivity as well as bendability—two parameters that are advantageous for mounting 3D microelectrode device 400 upon a live tissue surface susceptible to movement.

These features, as well as other advantageous features, will be described below using additional figures.

Figure 5:
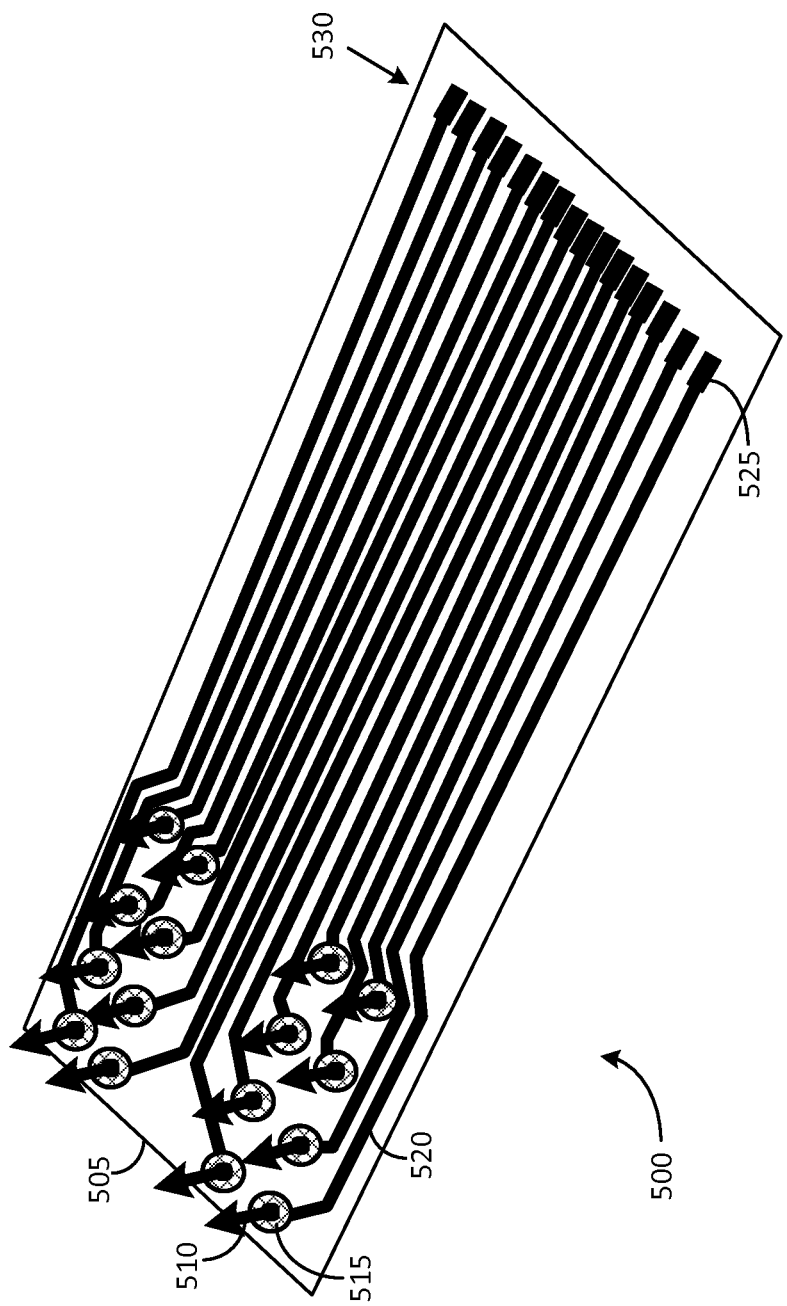
FIG. 5 shows an exemplary embodiment of a 3D microelectrode device in accordance with an embodiment of the present invention.

Towards this end, attention is drawn to FIG. 5, which shows a few constituent elements of a 3D microelectrode device 500 in accordance with an embodiment of the present invention. Though this embodiment includes a number of microelectrodes arranged in an array layout format, it will be understood that in other embodiments, a single microelectrode may be used, or two or more microelectrodes may be arranged in a non-array (or array) layout format. Furthermore, the layout formats of the microelectrodes as well as the form factor and shape of the substrate upon which the microelectrodes are located may be selected on the basis of the organ upon which the 3D microelectrode device is to be placed. For example, an elongated layout format for the microelectrodes and/or the substrate may be used for an organ having a longitudinal shape, and an irregularly shaped layout format for the microelectrodes and/or the substrate may be used for an organ having and irregular shape and/or an irregular surface contour. In one example implementation, the microelectrodes are arranged as a 2×2 array occupying an area of about 2 mm$^2$, with an inter-electrode spacing of about 200 μm.

In the embodiment shown in FIG. 5, 3D microelectrode device 500 includes a flexible substrate 505 upon which is located an array of microelectrodes. Substrate 505 is a flexible substrate containing PDMS and allows 3D microelectrode device 500 to be conformably placed upon live muscle/tissue. For purposes of describing certain details about the array of microelectrodes, a single microelectrode 510 will be used hereon as a matter of convenience. However, it will be understood that the description is equally applicable to other similar microelectrodes and elements of 3D microelectrode device 500 as well.

Microelectrode 510, which may be formed of a material that is either a good conductor of electrical signals (for example, a metal) or of a material that is at least a partially good conductor of electrical signals (for example, a polymer), is anchored in a pad 515 that is formed of conductive poly-dimethyl siloxane (cPDMS) material.

When 3D microelectrode device 500 is placed in operative condition, electrical signals coupled into microelectrode 510 (from tissue/muscle in which microelectrode 510 is embedded) are transferred from microelectrode 510 directly into the cPDMS material contained in pad 515 and from thereon, into conductive track 520 (which also contains cPDMS material) and to a cPDMS pad 525 that is one pad in a set of cPDMS pads 530.

Prior art techniques of attaching a microelectrode to a substrate (even a flexible substrate) include soldering the microelectrode to a metal pad, or attaching the microelectrode to the pad using an epoxy compound. In contrast, and in accordance with an embodiment of the present invention, a base portion of microelectrode 510 is shaped in a manner that accommodates anchoring of microelectrode 510 directly in the cPDMS material contained in pad 515 without requiring solder or epoxy compounds.

The cPDMS material contained in pad 515 not only anchors microelectrode 510, but has a Young's Modulus index that permits the base portion of microelectrode 510 to pivot in various directions, thereby allowing microelectrode 510 to bend in accordance with the contours of a muscle/tissue surface and/or in order to accommodate movement in a live muscle/tissue surface. Movement in the muscle/tissue surface may be further accommodated by selecting a suitable microelectrode 510 having a flexible property such as a polymer microelectrode, for example.

Similar to pad 515, conductive track 520 also contains cPDMS and accommodates 3D flexing and bending of 3D microelectrode device 500 while providing good conductivity to electrical signals.

Figure 6:
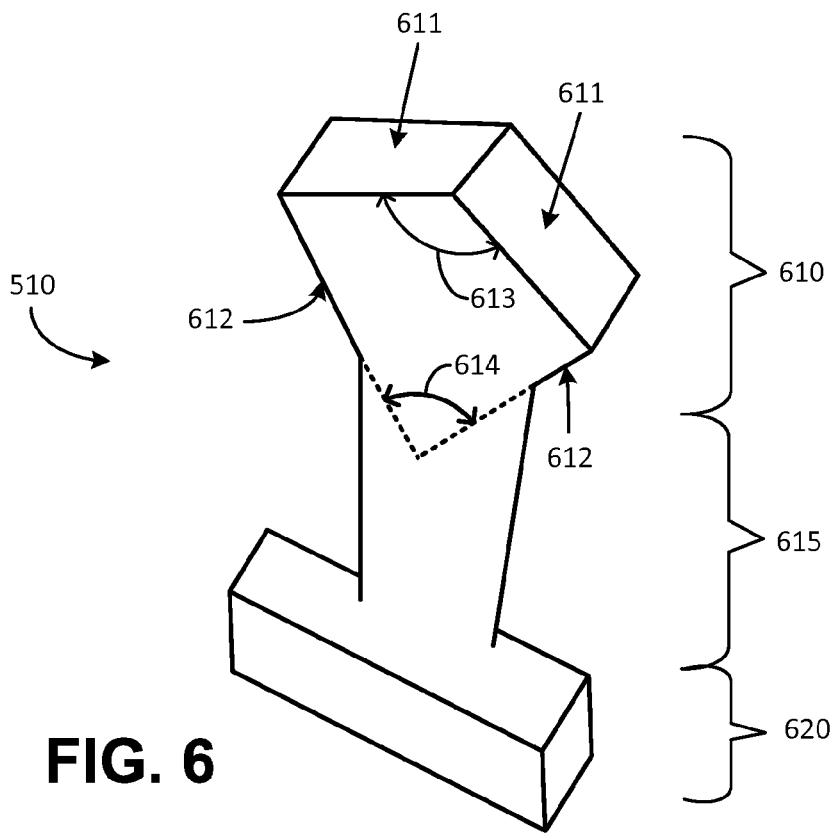
FIG. 6 shows a first exemplary insertable tip that is a part of a 3D microelectrode device in accordance with an embodiment of the present invention.

FIG. 6 shows a first example embodiment of a microelectrode 510 in accordance with an embodiment of the present invention. Microelectrode 510, which may be a micromachined or micro-stamped part fabricated from a sheet of metal, includes an insertable tip 610, a longitudinal portion 615, and a base portion 620. Insertable tip 610 is not only shaped to penetrate muscle/tissue but also to provide an anchoring action after penetration. More particularly, a leading portion 611 has a pointed shape that penetrates muscle/tissue and a trailing portion 612 that hinders withdrawal of microelectrode 510 from muscle/tissue.

In this example embodiment, insertable tip 610 has a diamond-shaped cross-sectional profile with leading portion 611 constituting two sides of the diamond-shaped profile. Trailing portion 612 constitutes two other sides of the diamond-shaped profile. Angular displacement 613 may be selected on the basis of a desired "pointiness" for penetration purposes into various types of muscle and/or tissue, while angular displacement 614 may be selected on the basis of a desired level of anchoring in various types of muscle and/or tissue without causing excessive damage when microelectrode 510 is withdrawn from the muscle/tissue.

Longitudinal portion 615 has a length that is selected on the basis of a desired protrusion distance from a top surface of flexible substrate 505 (shown, for example, in FIG. 5). The protrusion distance may be selected on the basis of a desired penetration depth into tissue or muscle. Base portion 620 is anchored in the cPDMS material contained in pad 515 (shown, for example, in FIG. 5).

Figure 7:
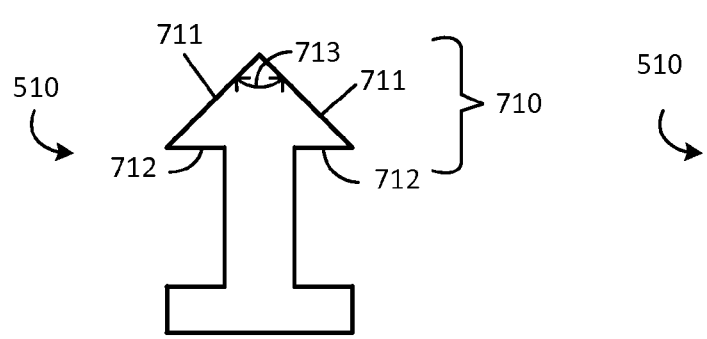
FIG. 7 shows a second exemplary insertable tip that is a part of a 3D microelectrode device in accordance with an embodiment of the present invention.

FIG. 7 shows a second example embodiment of a microelectrode 510 in accordance with the invention. In contrast to the diamond-shaped profile of insertable tip 610 described above, in this second embodiment, insertable tip 710 is an arrowhead tip having a substantially triangular shape. The surface area of insertable tip 710 may be selected to provide a desired amount of contact between microelectrode 510 and various types of muscle and/or tissue. Correspondingly, the overall dimensions of microelectrode 510 may be tailored on the basis of penetration parameters and contact parameters associated with various types of muscle and/or tissue, and/or on the basis of the size and shape of the muscle and/or tissue.

The leading portion 711 of insertable tip 710 has a suitable angular displacement 713 between two sides of the triangle. Angular displacement 713 may be selected on the basis of a desired level of penetrability and/or ease of penetrability into various types of muscle and/or tissue.

In contrast to the shape of trailing portion 612 described above, the trailing portion 712 of insertable tip 710 has a substantially straight configuration. More particularly, trailing portion 712 is oriented substantially parallel to a tissue surface when leading portion 711 has penetrated the tissue surface.

Figure 8:
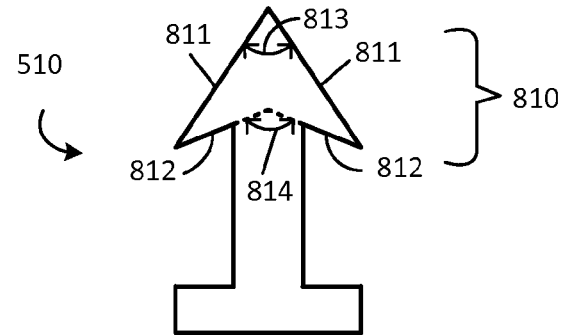
FIG. 8 shows a third exemplary insertable tip that is a part of a 3D microelectrode device in accordance with an embodiment of the present invention.

FIG. 8 shows a third example embodiment of a microelectrode 510 in accordance with the invention. Similar to insertable tip 710, which is an arrowhead tip having a substantially triangular shape, insertable tip 810 also is an arrowhead tip having a substantially triangular shape. However, the angular displacements in insertable tip 810 are different than those in insertable tip 710.

Angular displacement 813 may be selected on the basis of a desired level of penetrability and/or ease of penetrability into various types of muscle and/or tissue.

In contrast to the shape of trailing portion 712 described above, the trailing portion 812 has an angular orientation that may be defined on the basis of angular displacement 814. Angular displacement 814 may be selected on the basis of a desired level of anchoring in various types of muscle and/or tissue without causing excessive damage when microelectrode 510 is withdrawn from the muscle/tissue.

It can be understood that angular displacement 814 is oriented in an opposing direction to angular displacement 614 (described above with reference to the embodiment shown in FIG. 6), thereby providing a higher level of anchoring than angular displacement 614.

However, angular displacement 814 is oriented in the same direction as angular displacement 813. The sharp tips at the vertices of leading portion 811 and trailing portion 812 provide additional anchoring when microelectrode 510 is inserted into muscle and/or tissue.

Microelectrode 510 also includes a base portion 820 that may be provided in different shapes. In addition to the shape shown in FIG. 8, a different shape is shown in FIGS. 9 and 10, which will now be used to describe one example of a manufacturing process for manufacturing microelectrode 510.

Figure 9A:
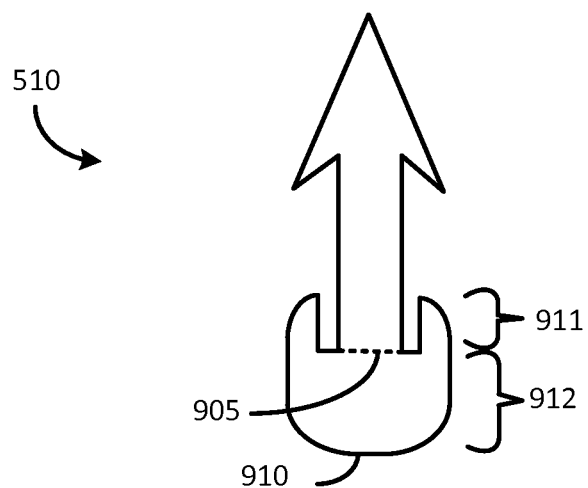
FIG. 9A shows a microelectrode as viewed after completion of a first step in an example manufacturing procedure of the microelectrode in accordance with an embodiment of the present invention.

FIG. 9A shows a microelectrode 510 viewed after completion of a first step in an example manufacturing procedure of microelectrode 510 in accordance with an embodiment of the present invention. In this example, microelectrode 510 has a base portion 910 that includes a major portion 912 that is substantially square or rectangular in shape (with rounded corners) and a pair of ears 911 extending from major portion 912. The first step in this example manufacturing procedure is carried out by micro-fabrication of metal parts. For example, a 5"×5" sheet of metal may be used in conjunction with various techniques such as photo chemical milling, photo-definition, etching, laser-cutting, stamping, or the like, to fabricate the microelectrode 510 shown in FIG. 9A. Dotted line 905 represents an axis along which major portion 912 may be folded with respect to the pair of ears 911 as described below using FIG. 9B.

Figure 9B:
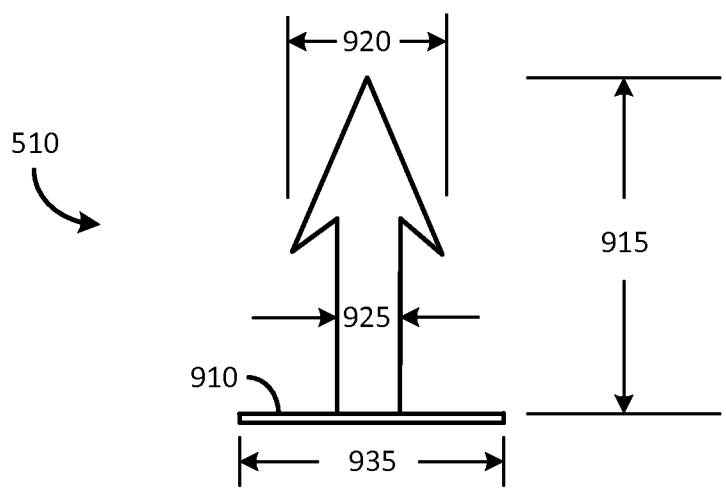
FIG. 9B shows the microelectrode of FIG. 9A as viewed after completion of a second step in the example manufacturing procedure of the microelectrode in accordance with an embodiment of the present invention.
Figure 10:
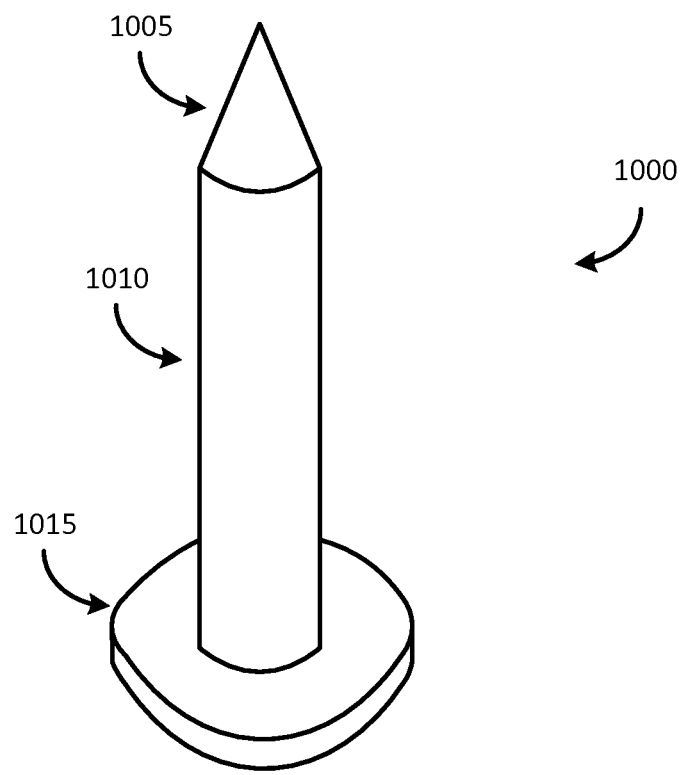
FIG. 10 shows an exemplary stainless steel microneedle in accordance with an embodiment of the present invention.

FIG. 9B shows microelectrode 510 viewed after completion of a second step in the example manufacturing procedure of microelectrode 510 in accordance with an embodiment of the present invention. The second step involves bending microelectrode 510 along dotted line 905 shown in FIG. 9A. The bending may be carried out using a suitable micro-press or other arrangement. In terms of dimensions, a height 915 of microelectrode 510 may be selected in accordance with various implementations. For example, in a first example implementation, height 915 is about 1 μm, while in a second implementation, height 915 is about 5 mm. Width dimensions may also be selected in accordance with various implementations. For example, in a first example implementation, width 920 is greater than width 925, but less than width 935. In a second example implementation, width 920 is greater than width 925 as well as width 935. In a third example implementation, width 925 is less than width 920 as well as width 935.

The flat-bottom configuration of major portion 912 after the bending procedure permits microelectrode 510 to be placed in an upright position embedded in the cPDMS material. When so embedded in the in the cPDMS material, the longitudinal portion and the insertable tip of microelectrode 510 can flex in at least two directions without detaching microelectrode 510 from the cPDMS material.

It will be understood, that in contrast to microelectrode 510 (described above with reference to FIGS. 9A and 9B), which is fabricated from a metal sheet, in an alternative embodiment, microelectrode 510 may be a micromachined stainless steel microneedle or an electrochemically milled stainless steel microneedle. An illustrative example of a stainless steel microneedle 1000 is shown in FIG. 10. The stainless steel microneedle 1000 may have a minimum sharpness of a pointed tip 1005 that is less than or equal to about 1 μm and a diameter of a longitudinal portion 1010 in the order of a few micrometers. Base portion 1015, may have various shapes, including circular, oval, square, rectangular, or the like, and may also include various protruding portions (not shown) such as fingers and ears extending out from a central major portion. In the example embodiment shown in FIG. 10, stainless steel microneedle 1000 has a tapered insertion tip with no trailing edges. However, in other embodiments, stainless steel microneedle 1000 may have an arrowhead tip shape that includes leading and trailing edges and/or tapered leading and trailing slopes. In another embodiment of the present invention, the microneedle is constructed of a material other than stainless steel.

Figure 11:
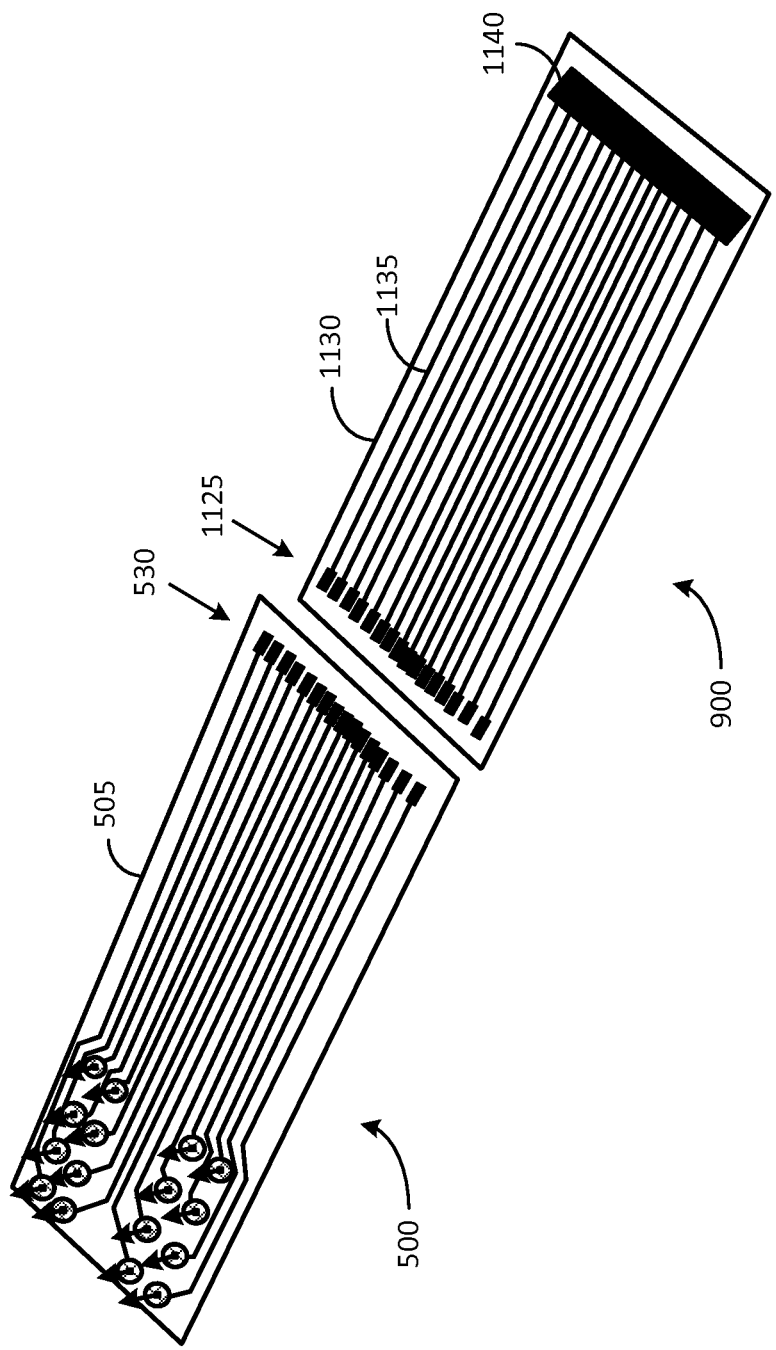
FIG. 11 shows a 3D microelectrode device configured for coupling to an extender assembly using a lamination process in accordance with an embodiment of the present invention.

FIG. 11 shows 3D microelectrode device 500 configured for coupling to an extender assembly 900 using a lamination process. Extender assembly 900 may include a rigid substrate such as in a printed circuit board (PCB) extender assembly or may include a flexible substrate such as in a Kapton extender assembly. For convenience of description, extender assembly 900 shown in FIG. 11 will be interpreted as a flexible Kapton assembly and will be described below accordingly. However, one of ordinary skill in the art will understand how this description may be applied to a PCB assembly as well.

The set of cPDMS pads 530 is a part of 3D microelectrode device 500, while a corresponding set of metal pads 1125 is a part of PCB assembly 900. The cPDMS-pad-to-metal-pad contact is established by a lamination process that is described below in more detail. In particular, flex circuit based lamination provides desirable advantages in terms of stretchability and compatibility for connecting to electronic circuitry.

The set of metal tracks (including metal track 1135) as well as the set of metal pads 1125 on extender assembly 900 may be provided using standard computer-aided-design (CAD) processes for defining the tracks on the Kapton substrate 1130, followed by additive processes (lift-off techniques, for example) or subtractive processes (metal etching, for example).

In one example implementation using additive definition, a photoresist layer of about 6 μm is spin coated onto a Kapton substrate 1130 (of about 12.5 μm in thickness) that is immobilized on a glass wafer (used as a carrier). The photoresist layer is exposed using UV lithography (for example, I line with 365 nm wavelength and 1150 mJ/cm$^2$ dose) and the pattern is then developed to define the metal tracks on the Kapton substrate 1130.

After a short de-scum process to remove resist residue utilizing oxygen plasma (using a Reactive Ion Etch tool, for example), a metal stack (50 nm of Ti or Cr and 500 nm of Au, for example) is evaporated using a directional deposition tool (such as an E-Beam Evaporator). After the evaporation the photoresist is lifted off the Kapton substrate 1130 using a soak in an acetone bath leaving behind the metal track patterns.

Lamination of the 3D microelectrode device 500 and the extender assembly 900, more particularly, set of cPDMS pads 530 and the corresponding set of metal pads 1125 may be carried out as described below. Metal pads 1125 may be formed of any suitable metal, such as, for example, gold, copper, or metal compounds. The same laminating procedure may be used to attach a connector 1140 to Kapton substrate 1130.

Figure 12:
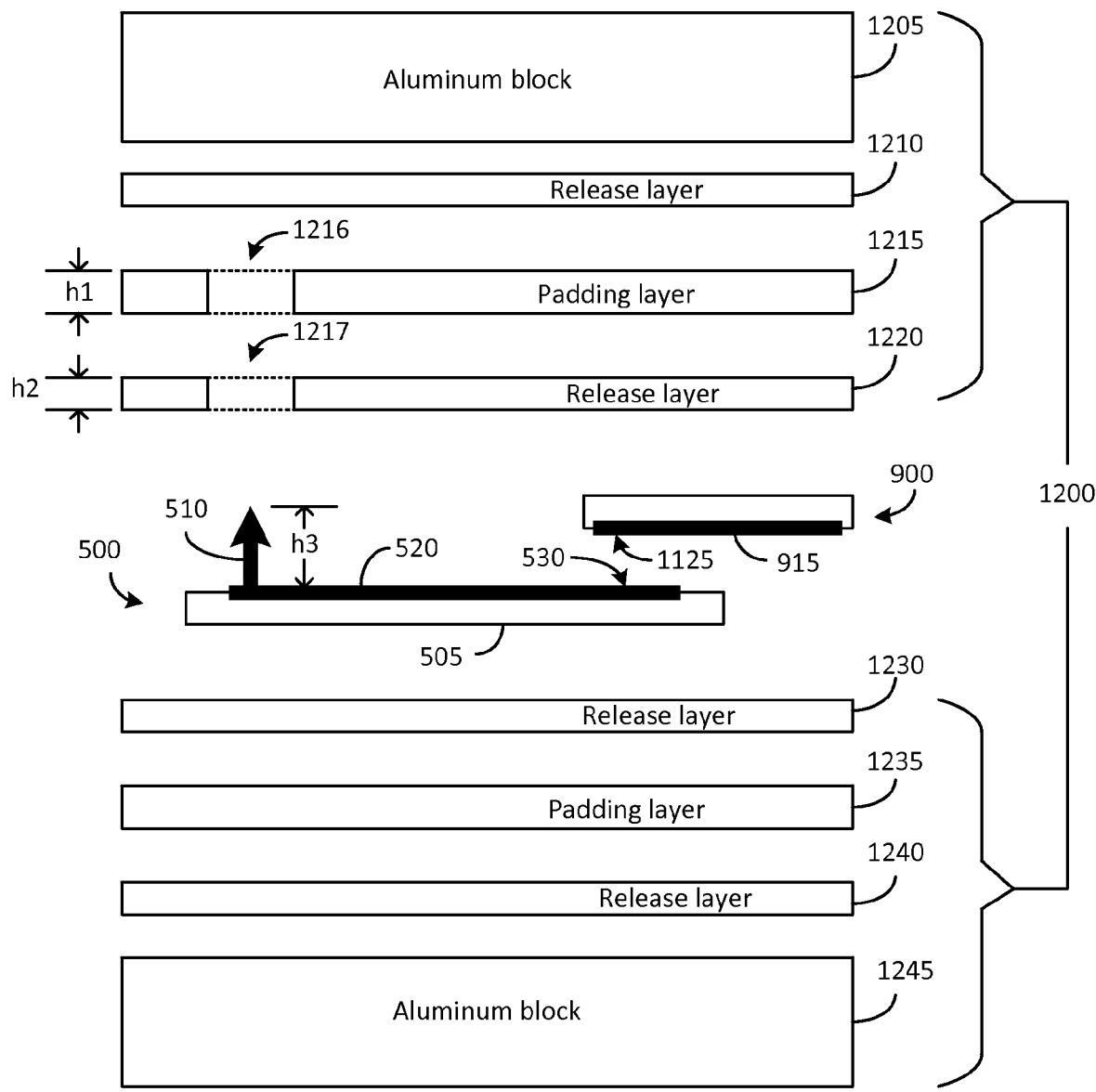
FIG. 12 shows a lamination apparatus for executing a lamination process in accordance with an embodiment of the present invention.

The surfaces of Kapton substrate 1130 and flexible substrate 505 are treated to a 1 minute oxygen plasma cycle prior to the lamination. This process activates the surfaces and improves the adhesion between the two substrates. A lamination stack, as shown in FIG. 12, is then prepared. An intermediate acrylic adhesive layer (12.5 μm thick) may be utilized to bind the two substrates together. The lamination may be performed at a temperature of about 275° F. and a pressure of about 750 psi. The acrylic adhesive reflows at such temperatures and binds the two materials involved.

The lamination bonding process creates a mechanical/chemical bond to bring together cPDMS/PDMS/Kapton and metal (gold, for example) in an intimate contact mode that provides mechanical integrity as well as electrical conductivity without the use of solder or epoxy adhesives. This lamination bonding process may be interpreted as a mechanical/chemical bonding process having two portions: a mechanical portion that brings the components together and holds them in place due to pressure being applied to the parts, and a chemical portion that is achieved due to the activation of both surfaces in oxygen plasma prior to the bonding. These two portions cooperatively bring the two surfaces with conductive materials (gold on Kapton and metal flakes in cPDMS) in contact with each other at a nanometer scale level (in contrast to various conventional meal-to-metal bonding processes.)

The chemical portion of the bonding constitutes an oxygen free radical bonding to another oxygen free radical as a result of excess free radicals being created during the oxygen plasma activation of the surfaces. An X-Ray Photoelectron Spectroscopy (XPS) study of the two surfaces provides an insight into the chemical nature of the bonding. As is known in the art, XPS is an analytical technique wherein a monochromatic beam of x-rays is directed into a sample in order to and detect the characteristics of electrons that are ejected from the sample. The energies and the number of electrons can be used to study not only the elements present on the sample surface but also their abundance and their chemical bonding state as well. Since the technique is highly surface sensitive (information at ~5 nm from the top of the surface can be gleaned from an XPS study), it can detect elements at very low concentrations. The XPS results are summarized in Table 1 shown below, which demonstrates an increase in oxygen content on all surfaces prior and post treatment of the surface using oxygen plasma. An increase in gold content on the Kapton surface and an increase in silicon content on the cPDMS surface are also observable from the results.

TABLE 1

XPS Results

| Material Composition | Native Material | Oxygen Plasma Treated |
|---|---|---|
| cPDMS | | |
| Carbon (%) | 46 | 27 |
| Oxygen (%) | 28 | 41 |
| Silicon (%) | 25 | 30 |
| Other Elements (%) | 1 | 2 |
| PDMS | | |
| Carbon (%) | 44 | 24 |
| Oxygen (%) | 26 | 48 |
| Silicon (%) | 29 | 27 |
| Other Elements (%) | 1 | 1 |
| Au/Kapton | | |
| Carbon (%) | 62 | 28 |
| Oxygen (%) | 19 | 19 |
| Gold (%) | 19 | 53 |
| Other Elements (%) | 0 | 0 |
| Kapton | | |
| Carbon (%) | 69 | 61 |
| Oxygen (%) | 20 | 30 |
| Other Elements (%) | 11 | 9 |

FIG. 12 shows a lamination apparatus 1200 for executing a lamination process to form a cPDMS-element-to-metal-element contact in accordance with an embodiment of the present invention. More particularly, lamination apparatus 1200 shown in FIG. 12 may be used for forming an electrically-conductive contact between the set of cPDMS pads 530 of 3D microelectrode device 500 and the corresponding set of metal pads 1125 of extender assembly 900.

Lamination apparatus 1200 has a sandwich structure that includes a pair of aluminum blocks 1205 and 1245, a first pair of release layers 1210 and 1240, a pair of padding layers 1215 and 1235, and a second pair of release layers 1220 and 1230. Each of the release layers may be selected of a material such as Teflon, so as to prevent adjacent layers from attaching to one another.

Padding layer 1215 includes an opening 1216 and has a thickness "h1" while release layer 1220 includes an opening 1217 and has a thickness "h2." 3D microelectrode device 500 is located between release layer 1220 and release layer 1230 such that microelectrode 510, which is an upright microelectrode having a height "h3," is aligned with the openings 1216 and 1217. Thicknesses "h1" and "h2 are selected to exceed "h3" and the size of openings 1216 and 1217 are selected to accommodate microelectrode 510 without touching the sides of openings 1216 and 1217 when microelectrode 510 is inserted into these openings during the lamination process. It will be understood that multiple openings may be provided when multiple microelectrodes are present in 3D microelectrode device 500.

Lamination apparatus 1200 allows execution of a compression procedure on the set of cPDMS pads 530 of 3D microelectrode device 500 and the corresponding set of metal pads 1125 of extender assembly 900 without adversely impacting microelectrode 510 (and other such microelectrodes).

Figure 13:
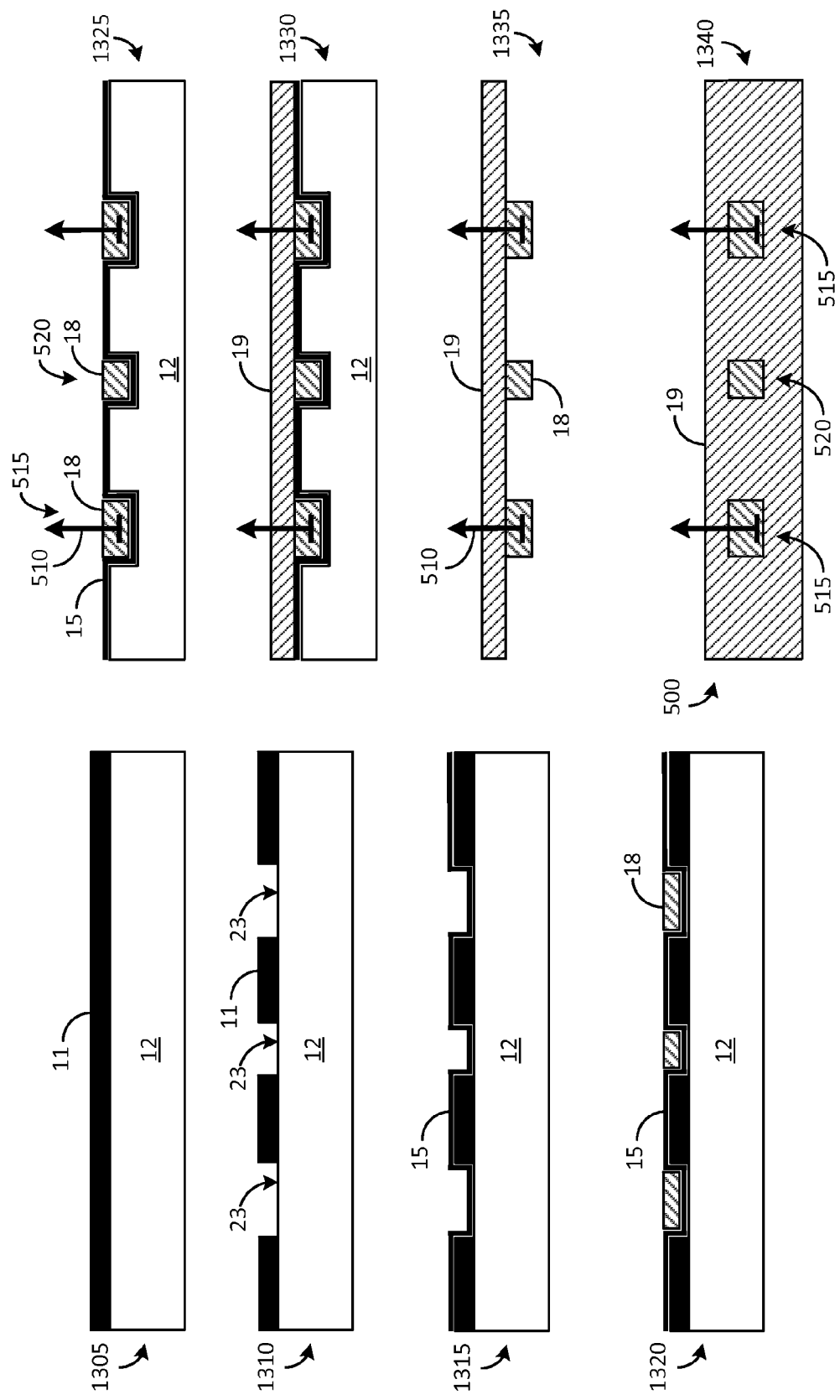
FIG. 13 illustrates an SU-8 based procedure for fabricating a 3D microelectrode device in accordance with an embodiment of the present invention.

FIG. 13 illustrates an SU-8 based procedure for fabricating a 3D microelectrode device in accordance with an embodiment of the present invention. In step 1305, a silicon wafer 12 is cleaned using piranha and Buffered Oxide Etch (BOE) solutions, followed by rinsing using deionized water. A layer of SU-8 material 11 is then spin coated upon the silicon wafer 12. In one example implementation, the SU-8 layer 11 is about 100 µm thick. The SU-8 layer 11 is then soft-baked to evaporate any solvent that may be present.

In step 1310, metal trace patterns (such as, for example, the tracks and pads of 3D microelectrode device 500 shown in FIG. 5), are provided in the SU-8 layer 11. This may be carried out by first generating a template using tools such as CAD and a high-resolution printer, followed by transferring the pattern from the template to the SU-8 layer 11 using UV photolithography (for example, using I line with 365 nm wavelength and 600 mJ/cm$^2$ dose). The pattern in the SU-8 layer 11 is then developed to form an SU-8 micromold. The SU-8 micromold includes areas 23 that correspond to a track or a pad in the finished product. As can be understood, track widths of around 1 µm, or even smaller, may be fabricated by using such a procedure.

In step 1315, a metal layer 15 is deposited on the SU-8 micromold using a sputter coater. Various types of metals and/or metal compounds such as chromium (Cr), titanium (Ti) and gold (Au), individually or in combination, may be used. In one example implementation, a combination of 50 nm of Cr and 500 nm of Au is used. The metal layer is operative as a separation layer during a demolding step later in the process. Additionally, a non-silicone mold release layer may be spray coated on to the SU-8 micromold.

In step 1320, cPDMS 18 (which is prepared as described below), is cast into the SU-8 micromold utilizing processes such as, for example, screen printing or squeegeeing. Air bubbles may then be removed using a suitable vacuuming operation. Upon completion of step 1325, the cPDMS tracks and pads of the 3D microelectrode device have been defined.

In step 1325, a microneedle (such as microneedle 510) is placed in a respective pad location (pad 515, for example) such that the base portion of microneedle 510 is encased in cPDMS 18. The placement may be carried out manually or by using a pick-and-place machine for placing multiple microneedles in multiple pad locations. After placement of the one or more microneedles, the sub-assembly is placed in an oven at approximately 160° C. for about 15 minutes in order to cure the cPDMS material, while ensuring that the base portion of each of the microneedles is completely encased inside cPDMS.

In step 1330, a layer of PDMS 19 is spun-coated on the upper surface of the sub-assembly such that the PDMS layer 19 covers the cPDMS material. In one example implementation, the PDMS layer 19 is about 300 µm thick.

The PDMS layer is then cured using an oven, for example. After the PDMS layer 19 is cured, the SU-8 micromold is detached as indicated in step 1335, and may be re-used for fabricating additional 3D microelectrode devices.

In step 1340, additional PDMS 19 is used to encapsulate the cPDMS pads and traces shown in step 1335. The resulting assembly constitutes the completed 3D microelectrode device 400.

The process described above, allows fabrication of various parts of 3D microelectrode device 400 down to miniature sizes in comparison to conventional processes that incorporate steps such as PCB patterning, etching, soldering and/or epoxy attachments of microelectrodes. The dimension of the cPDMS tracks fabricated by way of the process described above, may be characterized by a minimum width of around 1 µm. In one example implementation, the overall size of the 3D microelectrode device is about 7.5 mm×11.5 mm, with the microelectrodes having a diameter of about 37 µm with 425 µm spacing in a 4×4 grid arrangement.

Figure 14:
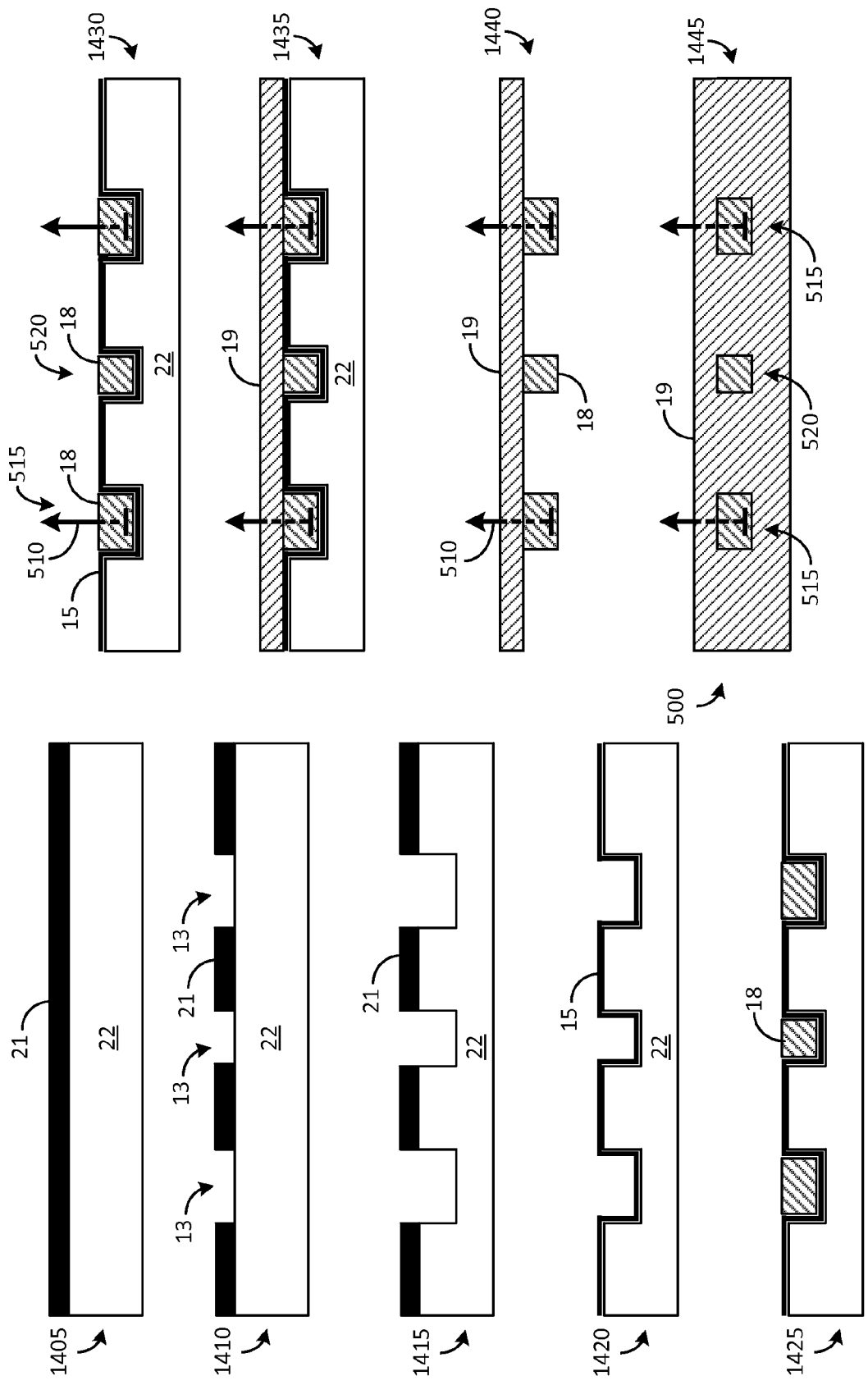
FIG. 14 illustrates a silicon based procedure for fabricating a 3D microelectrode device in accordance with an embodiment of the present invention.

FIG. 14 illustrates a silicon-based procedure for fabricating a 3D microelectrode device in accordance with an embodiment of the present invention. A silicon wafer 22 of a suitable dimension, for example, having a thickness of about 550 µm and 4 inch$^2$ to 6 inch$^2$ area, is provided. In step 1405, silicon wafer 22 is cleaned with piranha followed by a deionized water rinse. This is followed by cleaning with buffered hydrochloric acid and a deionized water rinse. A negative or positive photoresist layer 21 is then spin coated upon silicon wafer 22 to a thickness of about 6 µm.

In step 1410, metal trace patterns (such as, for example, the tracks and pads of 3D microelectrode device 500 shown in FIG. 5), are provided in the photoresist layer 21. This may be carried out by first generating a template using tools such as CAD and a high-resolution printer, followed by transferring the pattern from the template to the photoresist layer 21 using UV photolithography (for example, using I line with 365 nm wavelength and 1150 mJ/cm$^2$ dose). The pattern in the photoresist layer 21 is then developed to form a micromold. The micromold includes areas 13 that correspond to a track or a pad in the finished product.

In step 1415, the exposed silicon regions 23 are etched using a deep reactive ion etch (DRIE) process. The etching process is controlled such the sidewalls are smooth and almost perpendicular to a depth of about 100 µm. After the etching process, photoresist layer 21 is removed with solvents or by utilizing a piranha clean.

Steps 1420, 1425, 1430, 1435, 1440 and 1445 are substantially similar to steps 1320, 1325, 1330, 1335, 1340 and 1345 described above with reference to FIG. 13.

Formulation of the cPDMS used in the fabrication processes described above (with reference to FIGS. 13 and 14 for example) will now be described in more detail. PDMS material (such as Sylgard 184™) and a curing agent are pre-mixed together at a 10:1 ratio. Silver particles are then combined with the pre-mixed PDMS at a 4:1 ratio, for example, to create a cPDMS mixture. Various other ratios may be selected on the basis of achieving a desired level of electrical conductivity along with a desired level of stretchability. The high temperature of the curing process described above with reference to FIGS. 13 and 14, reduces the volume of the cPDMS mixture by about 20%, thereby bringing the silver particles into greater contact with each other and further reducing the resistance of the heat-treated material.

In summary, this disclosure describes various embodiments of a 3D microelectrode device that can be used for live tissue applications. The disclosure further describes a few example methods of fabricating such a 3D microelectrode device. The device, which includes a flexible substrate containing poly-dimethyl siloxane (PDMS), may be fabricated in a miniature form factor suitable for attachment to a small organ such as a lateral gastrocnemius muscle of a live rat. In addition to providing a miniaturized, conformable attachment, the device provides an anchoring action via one or more microelectrodes, each having an insertable tip particularly shaped to provide the anchoring action. Furthermore, a base portion of each of the microelectrodes is embedded inside conductive poly-dimethyl siloxane (cPDMS). The cPDMS is contained in a pad that is coupled to a conductive track embedded in the flexible substrate. Embedding of the base portion inside the cPDMS material not only allows the microelectrode to bend in various directions, but also provides good electrical conductivity while eliminating the need for attachment processes using solder or epoxy adhesives.

Persons of ordinary skill in the art will appreciate that though the devices and methods in accordance with the embodiments of the present invention have been described by means of specific embodiments and applications thereof, it is understood that numerous modifications and variations could be made thereto without departing from the spirit and scope of the disclosure.

Accordingly, it is to be understood that the inventive concept is not to be limited by the specific illustrated embodiments, but only by the scope of the appended claims. The description may provide examples of similar features as are recited in the claims, but it should not be assumed that such similar features are identical to those in the claims unless such identity is essential to comprehend the scope of the claim. In some instances the intended distinction between claim features and description features is underscored by using slightly different terminology.

The invention claimed is:

1. An implantable device comprising:
a flexible substrate configured to provide three-dimensional conformance with a live organ, muscle, or tissue susceptible to movement;
at least one track embedded in the flexible substrate for conducting an electrical signal, the track comprising conductive poly-dimethyl siloxane (cPDMS) material; and
at least one microelectrode comprising a base portion, a longitudinal portion, and an insertable tip, the base portion having a shape configured for anchoring the base portion in the cPDMS material, and the insertable tip having a leading portion configured for penetrating an outer surface of the organ, muscle, or tissue.

2. The device according to claim 1, wherein the insertable tip has a trailing portion having a shape configured for anchoring the microelectrode to the organ, muscle, or tissue.

3. The device according to claim 2, wherein the insertable tip is an arrowhead tip located at one end of the longitudinal portion, and the base portion is located at an opposing end of the longitudinal portion.

4. The device according to claim 3, wherein the trailing portion of the arrowhead tip is configured to be oriented substantially parallel to the outer surface of the organ, muscle, or tissue when the leading portion of the arrowhead tip has penetrated the outer surface of the organ, muscle, or tissue.

5. The device according to claim 3, wherein the trailing portion of the arrowhead tip is configured to be oriented at an angle to the outer surface of the organ, muscle, or tissue when the leading portion of the arrowhead tip has penetrated the outer surface of the organ, muscle, or tissue, the angle selected to provide a hindering action when the arrowhead tip is withdrawn through the outer surface of the organ, muscle, or tissue.

6. The device according to claim 1, wherein the microelectrode is a stainless steel microneedle and the flexible substrate comprises poly-dimethyl siloxane (PDMS) material.

7. The device according to claim 6, wherein the stainless steel microneedle is one of a laser micromachined stainless steel microneedle or a electrochemically-milled stainless steel microneedle having a minimum sharpness that is less than or equal to about 1 µm, and wherein a minimum width of the track is about 1 µm.

8. The device according to claim 6, wherein the flexible substrate, the track, and the stainless steel microneedle are included in an implantable package configured to be inserted under the tissue surface.

9. The device according to claim 8, wherein the flexible substrate included in the implantable package is selected for placement of the implantable package on at least one of a kidney or a brain of a rat.

10. The device according to claim 8, wherein the flexible substrate included in the implantable package is selected for placement of the implantable package on a lateral gastrocnemius muscle of a rat.

11. The device according to claim 6, wherein the implantable device is configured to interface with a device for containing and testing cells in-vitro.

12. The device according to claim 1, further comprising:
a plurality of signal-conducting tracks embedded in the flexible substrate, each of the plurality of tracks comprising conductive poly-dimethyl siloxane (cPDMS) material; and
a plurality of microelectrodes arranged in an array configuration, each of the plurality of microelectrodes comprising a base portion and a protruding portion, the base portion having a shape configured for anchoring the microelectrode in the cPDMS material, and the protruding portion having a shape configured for penetrating the outer surface of the organ, muscle, or tissue and for anchoring the implantable device in the organ, muscle, or tissue.

13. The device according to claim 12, wherein the base portion comprises a substantially planar surface oriented orthogonal to a longitudinal axis of the protruding portion.

14. The device according to claim 13, wherein the protruding portion comprises a longitudinal shaft having the base portion located at one end and a pointed tip located at an opposing end.

15. The device according to claim 14, wherein the longitudinal shaft has at least one of a circular, a rectangular, or a square cross-section, and wherein the pointed tip is an arrowhead tip.

16. The device according to claim 15, wherein the arrowhead tip includes at least one tapered corner for anchoring the arrowhead tip to the organ, muscle, or tissue.

17. The device according to claim 16, wherein each of the plurality of microelectrodes is one of a laser micromachined stainless steel microneedle or a electrochemically-milled stainless steel microneedle having a minimum sharpness of less than or equal to about 1 μm and wherein the flexible substrate comprises poly-dimethyl siloxane (PDMS) material.

18. The device according to claim 12, wherein the array configuration is at least a 2×2 array of microelectrodes arranged in an area of about 2 mm$^2$, with an inter-electrode spacing of about 200 μm.

* * * * *